United States Patent [19]
Arbogast et al.

[11] Patent Number: 5,800,563
[45] Date of Patent: Sep. 1, 1998

[54] IMPACT REDUCING PROSTHETIC PYLON

[75] Inventors: Robert E. Arbogast, Mt. Sterling; Eric K. Bartkus, Grove City; James M. Colvin, Hilliard; Sujatha Srinivasan, Mt. Sterling, all of Ohio

[73] Assignee: Ohio Willow Wood Company, Mount Sterling, Ohio

[21] Appl. No.: 577,141

[22] Filed: Dec. 22, 1995

[51] Int. Cl.[6] .................................................. A61F 2/62
[52] U.S. Cl. ........................ 623/35; 623/38; 267/141.2
[58] Field of Search .............................. 623/35, 38, 47, 623/50–53, 54, 55; 403/225, 226, 227; 267/141.2, 279, 293, 280, 281, 294

[56] References Cited

U.S. PATENT DOCUMENTS

| | | | |
|---|---|---|---|
| 383,569 | 5/1888 | Gault | 623/35 |
| 1,082,255 | 12/1913 | Apgar | 623/35 |
| 3,080,159 | 3/1963 | Omer | 267/293 X |
| 3,186,006 | 6/1965 | Miller | 623/36 |
| 4,085,832 | 4/1978 | Gaines et al. | 267/294 X |
| 4,364,128 | 12/1982 | Mummert | 623/38 X |
| 4,446,580 | 5/1984 | Furuya et al. | 623/53 |
| 4,995,598 | 2/1991 | Inghan | 267/294 X |
| 5,211,667 | 5/1993 | Danforth | 623/35 |
| 5,375,823 | 12/1994 | Navas | 267/195 |
| 5,425,780 | 6/1995 | Flatt et al. | 623/38 |
| 5,458,656 | 10/1995 | Phillips | 623/27 |

FOREIGN PATENT DOCUMENTS

| | | | |
|---|---|---|---|
| 140267 | 1/1948 | Australia | 267/279 |
| 587591 | 1/1929 | France | 623/53 |
| 548170 | 12/1957 | Italy | 267/293 |
| 984473 | 1/1983 | U.S.S.R. | 623/33 |

*Primary Examiner*—David H. Willse
*Attorney, Agent, or Firm*—Oblon, Spivak, McClelland, Maier & Neustadt, P.C.

[57] ABSTRACT

An impact reducing prosthetic pylon has a distal component which can be attached to a prosthetic foot and includes a housing within which the proximal component can slidably fit. A resilient bumper-like member formed of a foam is positioned within the housing and is compressed by the proximal component when the prosthesis is under a load. Relative rotation of the proximal and distal components is prevented, but a limited, resiliently damped rotation may be permitted.

16 Claims, 5 Drawing Sheets

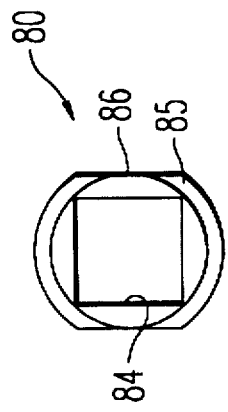
FIG. 6A
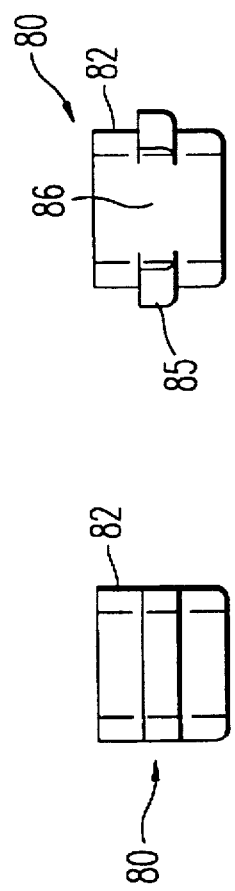
FIG. 6C
FIG. 6B
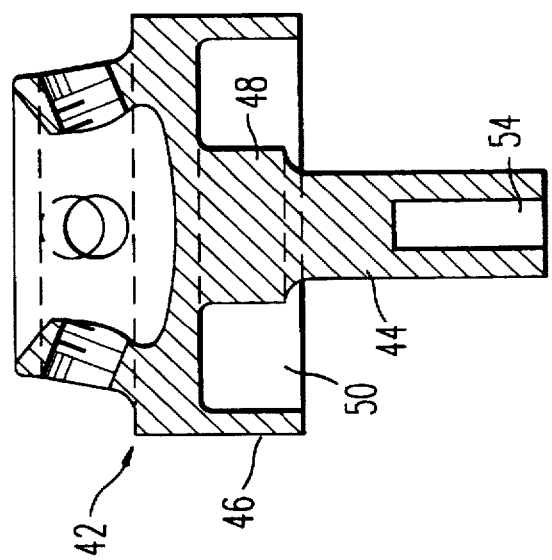
FIG. 5

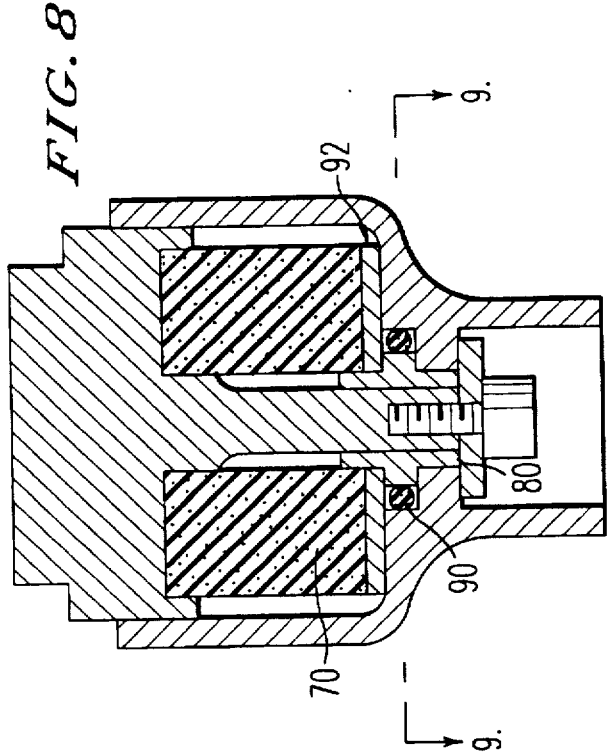
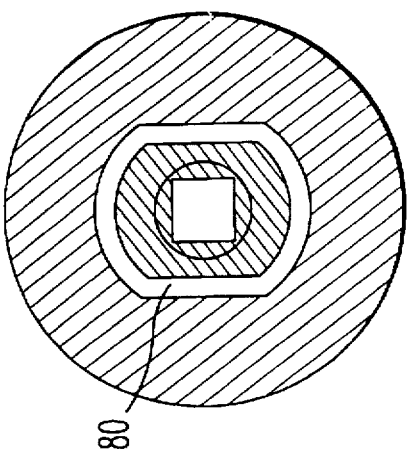
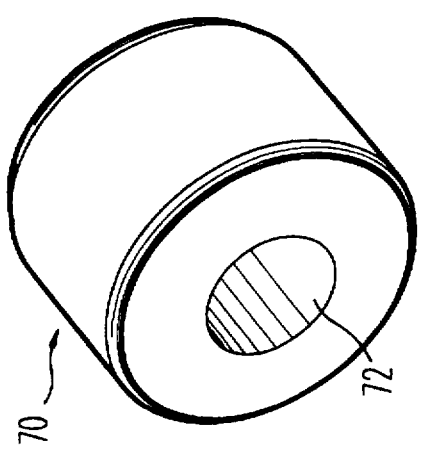

IMPACT REDUCING PROSTHETIC PYLON

BACKGROUND OF THE INVENTION

1. Field of the Invention

The present invention is directed to a prosthetic pylon. More particularly, it is directed to an impact reducing prosthetic pylon.

2. Description of the Related Art

A prosthetic pylon is the generally solid or tubular member connecting a prosthetic part such as a foot to an amputee's residual body part, typically through an intermediary part such as a socket for an amputee's residual limb. The pylon may be made of a variety of metals or composite materials, but most often is a thin-walled aluminum tube.

Such a rigid pylon has a drawback, however, in that it transmits the impact loads of running and jumping directly to the amputee's residual limb. Even walking can cause some dynamic type of loads to be transmitted to the residual limb, possibly resulting in shear of the amputee's skin, sores, skin blisters and wear and tear on the remaining anatomical structures. The conventional rigid metal pylon also transmits torsional stresses to the residual limb, for example, those resulting from the twisting of the foot during walking. This can also lead to shear on the skin of the residual limb, causing skin breakdowns and wear and tear on the remaining joints.

U.S. Pat. No. 5,458,656 discloses a prosthetic leg including a impact reducing pylon. The shock absorbing pylon of U.S. Pat. No. 5,458,656 has a pair of telescoping tubes connected by a composite leaf spring which is mounted longitudinally along the pylon and deflects outward as the tubes compress. However, whatever shock absorption this conventional pylon provides, it requires complex fabrication and, due to its bulkiness, is not totally compatible with standard prosthetic components. For example, it is extremely difficult to apply a finishing cosmetic foam cover over the pylon which appears natural. The pylon is also very expensive, putting it out of reach of many amputees who would benefit greatly from a shock absorbing device, and is relatively long compared to the average prosthesis, prohibiting its use on amputees with long residual limbs. Finally, it requires continuous maintenance, e.g., lubrication of components, and the need to hand fit the parts, preventing interchange of components in case of component breakage.

U.S. Pat. No. 4,883,493 also uses long telescoping tubes with a mechanical metal coil spring connecting the two tubes. It has an internal pneumatic cylinder for providing additional damping action. This device is also relatively long and heavy, and so has not been commercially successful.

SUMMARY OF THE INVENTION

It is an object of the present invention to provide an impact reducing prosthetic pylon which is compact in size, economical and simple to manufacture, and compatible with standard prosthetic components.

It is a further object of the invention to provide an impact reducing prosthetic pylon which reduces impacts by compression of a body of resilient material.

According to one aspect of the invention, the above and other objects are carried out by an impact reducing prosthetic pylon comprising a distal component attachable to a prosthetic body part, a proximal component attachable to a residual body part, and a joint between the distal and proximal components. The joint comprises a housing formed on at least one of the distal and proximal components, the other of the distal and proximal components being movably fitted in the housing such that it fits in the housing by a variable degree. A compressively resilient member is located in the housing and elastically limits the degree of fitting of the other of the components in the housing.

Preferably, the compressively resilient member comprises a foam body and the housing is formed at an end of the distal component.

Preferably, means are provided for limiting rotation of the distal component about the proximal component and for absorbing torsional stresses generated in the distal component and reducing transfer of the torsional stresses to the proximal component. Means may also be provided for preventing separation of the distal and proximal components.

According to a further feature of the invention, the above and other objects are accomplished by an impact reducing prosthetic pylon comprising a distal component having one end attachable to a prosthetic body part and having a housing at another end, the housing comprising a substantially annular wall centered substantially parallel to a line connected at the ends of the distal component. The annular wall defines a mouth comprising the other end of the distal component. A proximal component attachable to a residual body part is slidably fitted in the housing, and a compressively resilient member is disposed in the housing for resiliently limiting a degree of entry of the proximal component into the mouth of the housing, thereby reducing the transfer of impacts between the distal and proximal components.

The compressively resilient member may comprise a bumper-like body having a bore extending therethrough and the proximal part may comprise an adapter body having an upper adapter including means for attachment to a residual body part, a substantially annular sleeve closely fittable within the substantially annular wall of the housing such that the upper adapter extends from the mouth of the housing by a variable degree, and a projecting part which projects through the bore in the compressively resilient member and into the housing in a direction parallel to the axis of the substantially annular sleeve.

Means may be provided for limiting rotation of the distal component about the proximal component, the means for limiting rotation comprising a non-circular opening in a bottom wall of the housing and the projecting part slidably fitting in the non-circular opening, the projecting part having a non-circular shape mating with that of the non-circular opening.

Means may also be provided for preventing the adapter body from being removed from the housing and for absorbing torsional stresses generated in the distal component and reducing transfer of the torsional stresses to the proximal component. The means for absorbing torsional stresses may include a guide bushing mounted in the bottom wall of the housing and defining the non-circular opening therein, whereby the guide bushing rotates with the projecting part when the projecting part is fitted in the non-circular opening, and a resilient member positioned in the non-circular space between the guide bushing and the bottom wall of the housing for resiliently limiting the rotation of the guide bushing.

A low friction liner may be positioned between the substantially annular sleeve and the substantially annular wall, and the guide bushing may be formed of a low friction material.

The resilient material of the compressively resilient member comprises an elastomeric foam having high compressive strength and it is compressed such that the upper adapter is fully inserted in the mouth of the housing when the pylon is under load. Holes may be provided in the housing or proximal component for permitting air pressure equalization in the housing during movement of the proximal component therein.

A washer may be positioned between the compressively resilient member and the bottom wall of the housing for retaining the guide bushing in the bottom wall.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 is a sectional view of an upper adapter in the embodiment of FIG. 1;

FIGS. 6A–6C are respectively top, front and side views of a guide bushing according to an embodiment of the invention;

FIG. 7 is a perspective view of a resilient body according to an embodiment of the invention;

FIG. 8 is a sectional view of an impact reducing prosthetic pylon according to a further embodiment of the invention; and FIG. 9 is a sectional view along line IX—IX in FIG. 8.

DETAILED DESCRIPTION OF THE PREFERRED EMBODIMENTS

Figure 1:
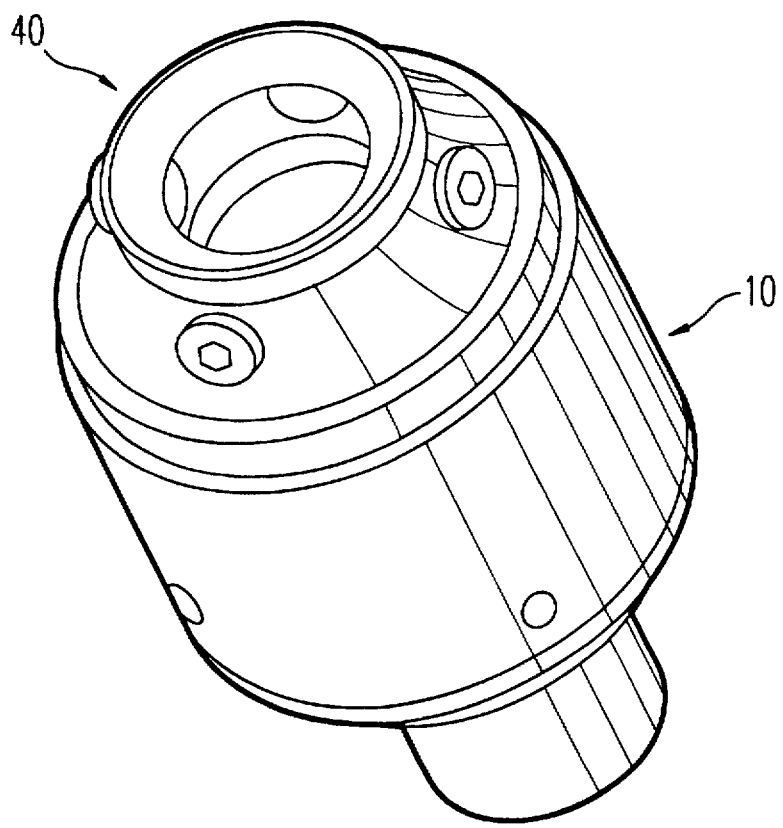
FIG. 1 is a prospective view of the impact reducing prosthetic pylon according to an embodiment of the present invention.

Nonlimiting embodiments of the present invention will now be described with reference to the accompanying figures, in which the same reference numerals will be used to designate the same or corresponding parts throughout the several views.

Referring to the first embodiment of FIGS. 1–7, an impact reducing prosthetic pylon according to the present invention comprises four major components: a distal component 10, a proximal component 40, a compressibly resilient member 70 and a guide bushing 80.

Figure 4C:
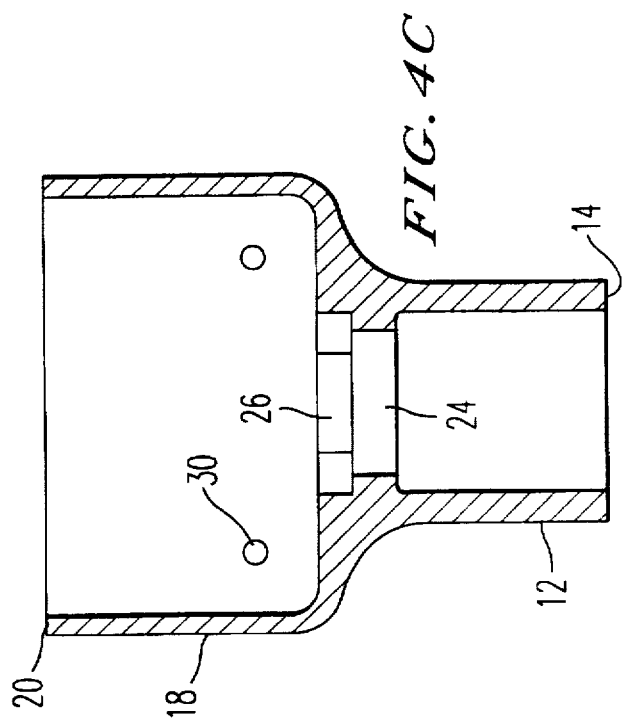
FIGS. 4A–4C are respectively top, front sectional and side sectional views of a distal component of an impact reducing prosthetic pylon according to the embodiment of FIG. 1.
Figure 4A:
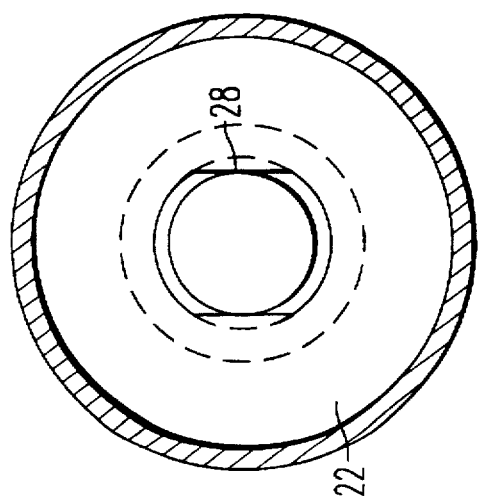
Figure 4B:
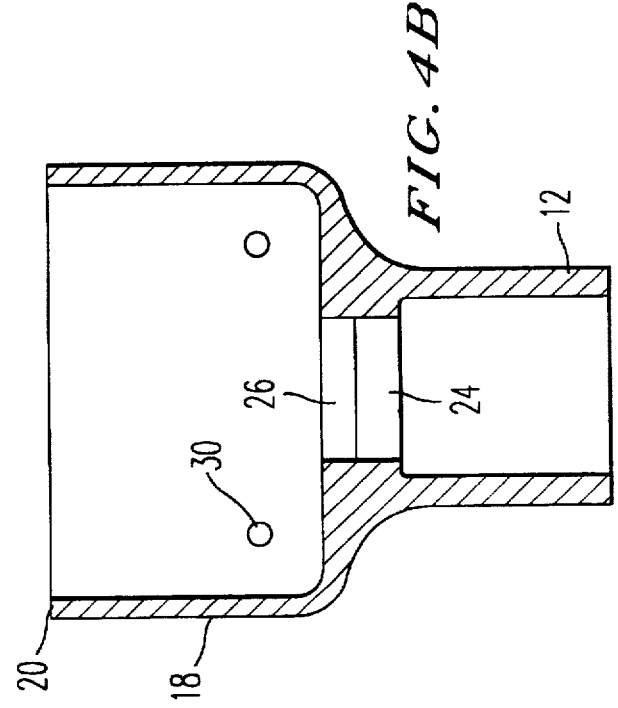

Referring especially to FIGS. 4A–4C, the distal component comprises a tube 12 of a conventional material such as aluminum. One end 14 of the tube may be connected to a prosthetic part such as a prosthetic foot (not shown). The length of the tube may vary and is tailored to a given amputee.

The other end of the distal component forms a housing 16 which is incorporated into the joint between the distal component 10 and the proximal component 40. The housing 16 takes the form of a substantially annular, in this case circular, wall 18 centered on the longitudinal axis of the tube 12. The wall 18 is unitary with the tube and has an open mouth 20 and a bottom wall 22. The bottom wall has a passage structure appropriate for accepting the guide bushing 80, which will be described further below. The passage structure includes a circular bore portion 24 in the bottom wall and a non-circular bore portion 26 having flats 28, both being centered on the longitudinal axis of the distal component.

Guide bushing 80 is formed of a low friction material such as acetyl or nylon and is primarily comprised of a cylindrical part 82 having a square section internal bore 84. A circumferentially extending shoulder 85 is formed integrally with the cylindrical part 82 and has a pair of flats 86 at circumferentially opposed positions. The cylindrical part and shoulder are sized such that the cylindrical part may be press fit or slip fit within the passage portion 24 of the distal component, and the circumferential shoulder 85 fits tightly within the passage portion 26 with the flats 86 aligning with the flats 28. The guide bushing 80 is therefore non-rotatably held within the distal component, with the square section bore 84 thereof being centered on, and parallel to, the longitudinal axis of the distal component 10.

A plurality of holes 30 are formed in the annular wall 18 of the housing 16, for a reason which will be explained below. The holes 30 may instead be vertical passages located in the upper adapter part of the proximal component 40.

Figure 3:
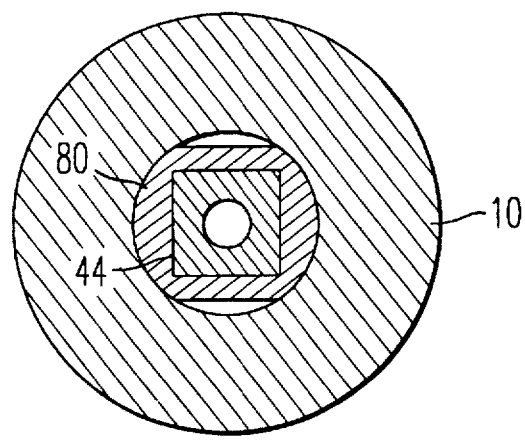
FIG. 3 is a section taken along the line III—III in FIG. 2.

The proximal component 40 is formed as an adapter body and may be made of metal, plastic or composite. It includes an upper adapter 42 which is conventional in construction and may include, e.g., set screws 43 for attachment to an amputee's stump socket or prosthetic knee. A projecting part 44 projects downward from the central part of the upper adapter, while a substantially annular sleeve 46 depends from the adapter body such that the projecting part 44 lies substantially on the central axis of the annular sleeve 46. The annular sleeve is sized so as to closely fit within the annular wall 18, while the projecting portion 44 has a square outer section which slidably fits within the square section of the guide bushing bore 84, as best seen in FIG. 3.

The adapter body may be fitted into the housing 16, projecting part 44 first. The projecting part 44 then slidably fits into the bore 84 of the guide bushing, while the annular sleeve 46 slides within, and is guided by, the interior of the annular wall 18 of the housing 16. The proximal component 40 is therefore able to slide axially within the housing, but not to rotate with respect thereto, while being guided by the bore 84 of the guide bushing and the annular wall 18 of the housing.

A cylindrical low friction sleeve 88 may be positioned within the housing between the annular wall 18 and the annular sleeve 46 for reducing friction during the sliding movement of the distal component.

A larger diameter base portion 48 of the projecting part 44 and the annular sleeve 46 together define an annular recess 50 (FIG. 5) whose inner diameter corresponds substantially to the outer diameter of the cylindrical part 82 of the guide bushing.

Figure 2:
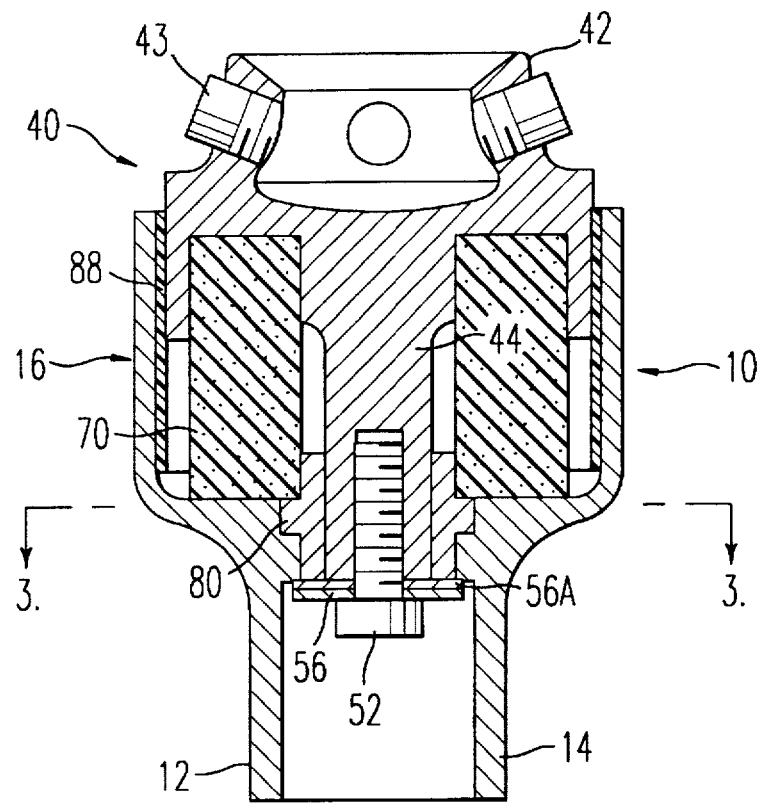
FIG. 2 is a section taken through an elevation of the impact reducing prosthetic pylon of FIG. 1.

The compressibly resilient member 70 may take the form of a cylindrical elastomeric foam body having an axial bore 72 extending therethrough. The inner and outer diameters of the foam body are such that it can be positioned within the housing 16 with the axis of the resilient member extending substantially colinear to the longitudinal axis of the distal component. In this case, the lower portion of the wall of the bore 72 fits tightly around the upper portion of the cylindrical part 82 of the guide bushing. The annular recess 50 of the proximal component 40 fits over the upper portion of the resilient member 70. As can be seen in FIG. 2, the projecting part 44 then extends through the bore 72 of the resilient member 70 and the bore 84 of the guide bushing 80, whose top portion is fitted within the bore 72 of the resilient member 70.

The resilient member 70 is formed of a foam having high compressive strength, high resistance to permanent deformation and the ability to compress by up to 50% of its original height without significantly bulging. An example of a material which may be used for the resilient member 70 is microcellular polyurethane foam. The compressive strength of the material of the resilient member 70 is important for supporting the weight of the amputee during active sports, while the high resistance to permanent deformation is important for preventing gaps which can cause play. The ability of the material to deflect by up to 50% of its free length without significant bulging is important for maximizing deflection while minimizing the physical size of the device.

The size and composition of the resilient member 70 is selected such that the upper adapter extends from the mouth of the housing when the prosthesis is not under load, i.e., when the weight of the amputee is not placed thereon. The set screws 43 are then accessible for adjusting the mounting of the prosthesis on the amputee. Conversely, the size and composition of the resilient member 70 is preferably selected such that when the weight of the amputee is placed on the prosthesis, the adapter body fully enters the housing 16 so as to minimize the length of the device.

As seen in FIG. 2, a screw 52 is threaded into a bore 54 extending from the bottom of the projecting part 44. The head of the screw presses a washer 56 onto the end of the projecting part. An elastomeric gasket 56 A may be positioned between the washer 56 and the bottom wall of the housing for absorbing impacts of the washer on the bottom wall. The diameter of the washer 56 is sufficiently large that it engages the lower surface of the bottom wall 22 of the housing around the passage portion 24 when the prosthesis is not under load, and thereby prevents the proximal component 40 from being further removed from the housing 16.

As the amputee walks using the prosthesis, the load of the amputee's weight is successively applied to, and released from, the distal component 10 via the proximal component 40. As this occurs, the proximal component 40 reciprocally slides within the housing 16 and while being guided by the engagement between the projecting portion 44 and the bore 84 of the low friction guide bushing 80, and by the sliding of the annular sleeve 46 within the annular wall 18, through the intermediary of the low friction sleeve 88. The resulting large surface area of contact reduces stresses resulting from bending forces and thereby reduces the likelihood of the proximal component binding during such movement. Additionally, the compression of the resilient member 70 during the application of load to the prosthesis resiliently absorbs the transmission of impacts to the residual limb of the amputee. The holes 30 permit pressure equalization in the housing as the proximal component slides therein.

During use, the rotation of the proximal component 40 relative to the distal component 10 is prevented by the mating square shapes of the elements 44 and 84. Since the guide bushing 80 is fixed within the distal component 10, it cannot rotate relative to the distal component and so prevents rotation of the proximal component. In the alternative embodiment shown in FIGS. 8 and 9, however, a limited, resiliently damped, rotation between the guide bushing 80 and the distal component 10 is permitted in order to absorb torsional stresses and prevent their transmission to the resilient limb of the amputee. As seen in FIGS. 8 and 9, the guide bushing 80 fits within the passage portion 24 with a slip fit, so that it can rotate about its axis. Additionally, the circumferential shoulder 85 is not press fitted within the passage portion 26, but is spaced therefrom so as to form an annular gap within which is positioned an elastomer spring 90. The guide bushing can therefore rotate by an angle limited due to the compression of the resilient elastomer spring 90 between the shoulder 85 and the wall of the passage portion 26.

The embodiment of the FIGS. 8 and 9 also has a metal washer 92 which may be positioned between the bottom of the resilient member 70 and the bottom wall 22 of the housing 16 in order to hold the guide bushing 80 in place during rotation. An elastomeric gasket (not shown) may be positioned between the washer 92 and the bottom wall 22 of the housing in order to minimize the impact of the metal washer 92 on the bottom wall 22 during the stroke of the proximal portion within the housing. This gasket may be made of a rubber based copolymer manufactured by DeRoyal Industries of Powell, Tenn.

The present invention therefore provides an impact reducing prosthetic pylon which produces reduced impact loading on the residual limb of the amputee. The ability of the resilient member 70 to deflect and absorb the impact forces reduces the trauma applied to the residual limb, including shear, tears and bruises.

It is a simple matter to remove the resilient member 70 by simply removing the screw 52 and lifting the adapter body out of the housing 16. Different resilient members of different stiffnesses are therefore easily interchangeable to allow the prosthetic pylon to be tailored to each patient.

The overall dimensions of the device are compact both in length and diameter. The short length is important to permit use by amputees having amputations near the ankle. The small diameter is important for cosmetic purposes since it is then easy to form a flexible foam cover about the prosthesis and thereby create a life-like shape.

Finally, the device is compatible with existing conventional prosthetic components and can be assembled with conventional tools. Low friction materials reduce wear and maintenance, and all of the components are easily replaced if needed. Both active and geriatric amputees can therefore use the device with greater comfort and reduced impact transmission.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. An impact reducing prosthetic pylon comprising:
 a distal component configured to be attached to a prosthetic body part;
 a proximal component attachable to a residual body part; and
 a joint between said distal and proximal components, said joint comprising:
  a) a housing formed at an end of said distal component, said proximal component being movably fitted in said housing such that said proximal component fits in said housing by a variable degree,
  b) a compressively resilient foam member located in said housing and elastically limiting a degree of fitting of said proximal component in said housing,
  c) means for limiting rotation of said distal component about said proximal component, d) means for absorbing torsional stresses generated in said distal component and reducing transfer of the torsional stresses to said proximal component, and e) means for preventing separation of said distal and proximal components, comprising a washer mounted to said proximal component and positioned at a bottom wall of said housing, further comprising an elastomeric gasket positioned between said washer and said bottom wall for absorbing impacts of said washer on said bottom wall.

2. The impact reducing prosthetic pylon of claim 1 wherein said foam member is formed of a microcellular foam.

3. The impact reducing prosthetic pylon of claim 1 wherein said foam member is formed of a microcellular polyurethane foam.

4. The impact reducing prosthetic pylon of claim 1 wherein said foam member is formed of a foam having high compressive strength, high resistance to permanent deformation and the ability to compress by up to 50% of original height without substantial bulging.

5. An impact reducing prosthetic pylon comprising:

a distal component having one end attachable to a prosthetic body part and having a housing at another end, said housing comprising a substantially annular wall centered substantially parallel to an axis of said distal component, said annular wall defining a mouth comprising said another end of said distal component;

a proximal component attachable to a residual body part, said proximal component being slidably fittable in said housing so as to vary the length of said pylon;

a compressively resilient foam member positioned in said housing for resiliently limiting a degree of entry of said proximal component into the mouth of said housing and reducing transfer of impact forces between said distal and proximal components;

means for limiting rotation of said distal component about said proximal component, wherein said compressively resilient member comprises a body having a bore extending therethrough, and said proximal component comprises an adapter body having an upper adapter including means for attachment to a residual body part, a substantially annular sleeve closely fittable within said substantially annular wall of said housing such that said upper adapter extends from the mouth of said housing by a variable degree, and a projecting part which projects through said bore in said compressively resilient member and into said housing in a direction parallel to an axis of said substantially annular sleeve, and wherein said means for limiting rotation of said distal component about said proximal component comprises a non-circular opening in a bottom wall of said housing, and said projecting part slidably fitting in said non-circular opening, said projecting part having a non-circular shape mating with that of said non-circular opening.

6. The impact reducing prosthetic pylon of claim 5 including means for preventing said adapter body from being removed from said housing.

7. The impact reducing prosthetic pylon of claim 6 including means for absorbing torsional stresses generated in said distal component and reducing transfer of the torsional stresses to the proximal component.

8. The impact reducing prosthetic pylon of claim 7 wherein said means for absorbing torsional stresses generated in said distal component and reducing transfer of the torsional stresses to the proximal component comprises:

a guide bushing rotatably mounted in the bottom wall of said housing and defining said non-circular opening therein, whereby said guide bushing rotates with said projecting part when said projecting part is fitted in said non-circular opening; and a resilient member positioned in a non-circular space between said guide bushing and the bottom wall of said housing for resiliently limiting rotation of said guide bushing.

9. The impact reducing prosthetic pylon of claim 8 wherein said guide bushing is formed of a low friction material.

10. The impact reducing prosthetic pylon of claim 8 including a washer positioned between said compressively resilient member and the bottom wall of said housing for retaining said guide bushing in the bottom wall.

11. The impact reducing prosthetic pylon of claim 5 including a low friction liner positioned between said substantially annular sleeve and said substantially annular wall.

12. The impact reducing prosthetic pylon of claim 5 wherein said compressively resilient member is compressed such that said upper adapter is fully inserted in the mouth of said housing when said pylon is under load.

13. The impact reducing prosthetic pylon of claim 5 wherein said resilient material of said compressively resilient member comprises an elastomeric microcellular foam having high compressive strength.

14. The impact reducing prosthetic pylon of claim 13 wherein said microcellular foam comprises a polyurethane foam.

15. The impact reducing prosthetic pylon of claim 5 including at least one hole in said pylon for permitting air pressure equalization in said housing during movement of said projecting part therein.

16. The impact reducing prosthetic pylon of claim 5 wherein said foam member is formed of a foam having high compressive strength, high resistance to permanent deformation and the ability to compress by up to 50% of original height without substantial bulging.

* * * * *